(12) United States Patent
Kim

(10) Patent No.: US 9,322,810 B2
(45) Date of Patent: Apr. 26, 2016

(54) ULTRASONIC TRANSDUCERS

(71) Applicant: SAMSUNG ELECTRONICS CO., LTD., Suwon-si (KR)

(72) Inventor: Dong-kyun Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 232 days.

(21) Appl. No.: 13/970,821

(22) Filed: Aug. 20, 2013

(65) Prior Publication Data

US 2014/0069194 A1 Mar. 13, 2014

(30) Foreign Application Priority Data

Sep. 11, 2012 (KR) .................. 10-2012-0100660

(51) Int. Cl.
G01N 29/28 (2006.01)
H04R 31/00 (2006.01)
B06B 1/02 (2006.01)
G10K 11/00 (2006.01)
A61B 8/00 (2006.01)

(52) U.S. Cl.
CPC .............. *G01N 29/28* (2013.01); *B06B 1/0292* (2013.01); *G10K 11/002* (2013.01); *H04R 31/006* (2013.01); *A61B 8/4483* (2013.01); *Y10T 29/49005* (2015.01)

(58) Field of Classification Search
CPC ...... G10K 11/002; A61B 8/00; A61B 8/4483; H04R 31/006; H04R 31/00; Y10T 29/49005; G01N 29/28; G01N 2291/106; G01N 29/2406

USPC ............. 73/632, 625, 626, 628, 641; 600/459
See application file for complete search history.

(56) References Cited

U.S. PATENT DOCUMENTS

| 6,876,127 | B2 * | 4/2005 | Mitsuoka et al. ............. 310/324 |
| 7,257,051 | B2 | 8/2007 | Thomenius et al. |
| 8,008,105 | B2 | 8/2011 | Huang |
| 8,742,646 | B2 * | 6/2014 | Wodnicki .............. B06B 1/0622 310/334 |
| 2003/0052419 | A1 * | 3/2003 | Ujiie et al. ..................... 257/787 |
| 2004/0190377 | A1 * | 9/2004 | Lewandowski ....... B06B 1/0292 367/174 |
| 2008/0067895 | A1 | 3/2008 | Adachi et al. |
| 2008/0134793 | A1 | 6/2008 | Woychik et al. |
| 2009/0140606 | A1 * | 6/2009 | Huang .................. B06B 1/0292 310/322 |
| 2010/0191108 | A1 * | 7/2010 | Sato ......................... A61B 8/06 600/437 |
| 2010/0255623 | A1 | 10/2010 | Huang |
| 2010/0280388 | A1 | 11/2010 | Huang |
| 2011/0071397 | A1 * | 3/2011 | Wodnicki .............. B06B 1/0629 600/459 |
| 2012/0103096 | A1 * | 5/2012 | Kandori .......................... 73/632 |

* cited by examiner

*Primary Examiner* — Laura Martin
*Assistant Examiner* — Suman K Nath
(74) *Attorney, Agent, or Firm* — Sughrue Mion, PLLC

(57) ABSTRACT

An ultrasonic transducer includes a plurality of transducer modules, a substrate on which each of the plurality of transducer modules is arranged, and a buffer member which buffers the movements of the upper portions of the transducer modules, wherein the buffer member is disposed on the substrate between the plurality of transducer modules and on the substrate outside of the plurality of transducer modules.

25 Claims, 6 Drawing Sheets

ULTRASONIC TRANSDUCERS

CROSS-REFERENCE TO RELATED APPLICATION

This application claims priority from Korean Patent Application No. 10-2012-0100660, filed on Sep. 11, 2012, in the Korean Intellectual Property Office, the disclosure of which is incorporated herein by reference in its entirety.

BACKGROUND

1. Field

The present disclosure relates to ultrasonic transducers, and more particularly, to ultrasonic transducers which have a multi-channel capacity and a large area.

2. Description of the Related Art

An equipment which is used for an ultrasonic image diagnosis may include an imaging device which performs signal processing of detected ultrasonic waves that are transmitted and attenuated by scanning a certain part of organisms or that are reflected from boundaries of mediums, each of which has a different acoustic impedance. Such equipment which is used for ultrasonic image diagnosis may include an ultrasonic probe device which transmits ultrasonic waves toward a target object and which receives reflected ultrasonic waves from the target object in order to obtain ultrasonic wave data. The ultrasonic probe device may also include an ultrasonic transducer that converts electrical energy into kinetic energy, or vice versa, within a range of ultrasonic frequencies.

An ultrasonic transducer includes several ultrasonic conversion elements that individually operate to generate one acoustic pulse. However, in order to obtain a high-resolution ultrasound image, the ultrasonic transducer with a multi-channel capacity and a large area which includes a large number of ultrasonic transducer elements is necessary. When this type of ultrasonic transducer is formed in an integral configuration, a main drawback is a falling manufacturing yield. Therefore, in order to solve this problem, a plurality of transducer modules that are large enough to secure a constant yield is manufactured, and the plurality of transducer modules are arranged on a substrate such as a Printed Circuit Board (PCB), and thus, the ultrasonic transducer having a multi-channel capacity and a large area results.

SUMMARY

Provided are ultrasonic transducers which have a multi-channel capacity and a large area.

Additional aspects will be set forth in part in the description which follows and, in part, will be apparent from the description, or may be learned by practice of the presented exemplary embodiments.

According to an aspect of one or more exemplary embodiments, an ultrasonic transducer includes a plurality of transducers; a substrate on which the plurality of transducers is arranged; and a buffer member which buffers movements of upper portions of the transducers, wherein the buffer member is disposed on the substrate between the plurality of transducers and on the substrate outside of the plurality of transducers.

Each of the plurality of transducers may include an ultrasonic transducer chip and a driver chip which is arranged underneath the ultrasonic transducer chip. Herein, the ultrasonic transducer chip may include a capacitive micromachined ultrasonic transducer chip, and the driver chip may include an application-specific integrated circuit (ASIC) chip.

The substrate may include a plurality of loaders in which the plurality of transducers are loaded, a plurality of adhesive parts which are arranged underneath the plurality of loaders such that top surfaces of the plurality of adhesive parts are adhered to undersurfaces of the plurality of transducers, and a support part which protrudes between the plurality of loaders and outside of the plurality of loaders. The support part may support the driver chips by being set to a lower height than a thickness of one of the plurality of loaders. In addition, the buffer member may buffer movements of the ultrasonic transducer chips because the buffer member is placed on top of the support part, and the buffer member may include at least one polymer-based material.

The buffer member may include at least one of two kinds of buffer members. One kind includes a first buffer part which is arranged on a side of at least one ultrasonic transducer chip, and the other kind includes a second buffer part which extends from the first buffer part toward an upper surface of at least one of the ultrasonic transducer chips.

The buffer member may include a first buffer member which is arranged between the ultrasonic transducer chips and a second buffer member which is arranged on an outside of the ultrasonic transducer chips. Herein, the first buffer member may include a first buffer part which is arranged on a side of at least one of the ultrasonic transducer chips and a second buffer part which extends from the first buffer part toward an upper surface of at least one of the ultrasonic transducer chips. In addition, the second buffer member may include a first buffer part which is arranged on a side of at least one ultrasonic transducer chip, a second buffer part which extends from the first buffer part toward an upper surface of at least one of the ultrasonic transducer chips, and a third buffer part which extends from the first buffer part toward an outside of the substrate.

One of the plurality of loaders may have a width which is wider than a width of a corresponding one of the plurality of transducers, and one of the plurality of adhesive parts may have a width which is narrower than the width of at least one of the plurality of loaders. The plurality of adhesive parts may be filled with adhesive materials. A plurality of out ports which connect the plurality of adhesive parts to an outside of the substrate may be formed in the substrate.

With respect to the plurality of adhesive parts, protrusions that protrude from a bottom of one of the plurality of adhesive parts may be formed. A top surface of at least one of the protrusions may adhere to an undersurface of at least one of the plurality of transducers. At least one of the protrusions may be integrally formed with the substrate. In addition, at least one of the protrusions may include a plurality of protrusions that are spaced at a predetermined spacing.

The substrate may include at least one of silicon, a glass, and a polymer-based material. The transducers may be arranged on the substrate in an m×n array, wherein each of m and n is a natural number.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1:
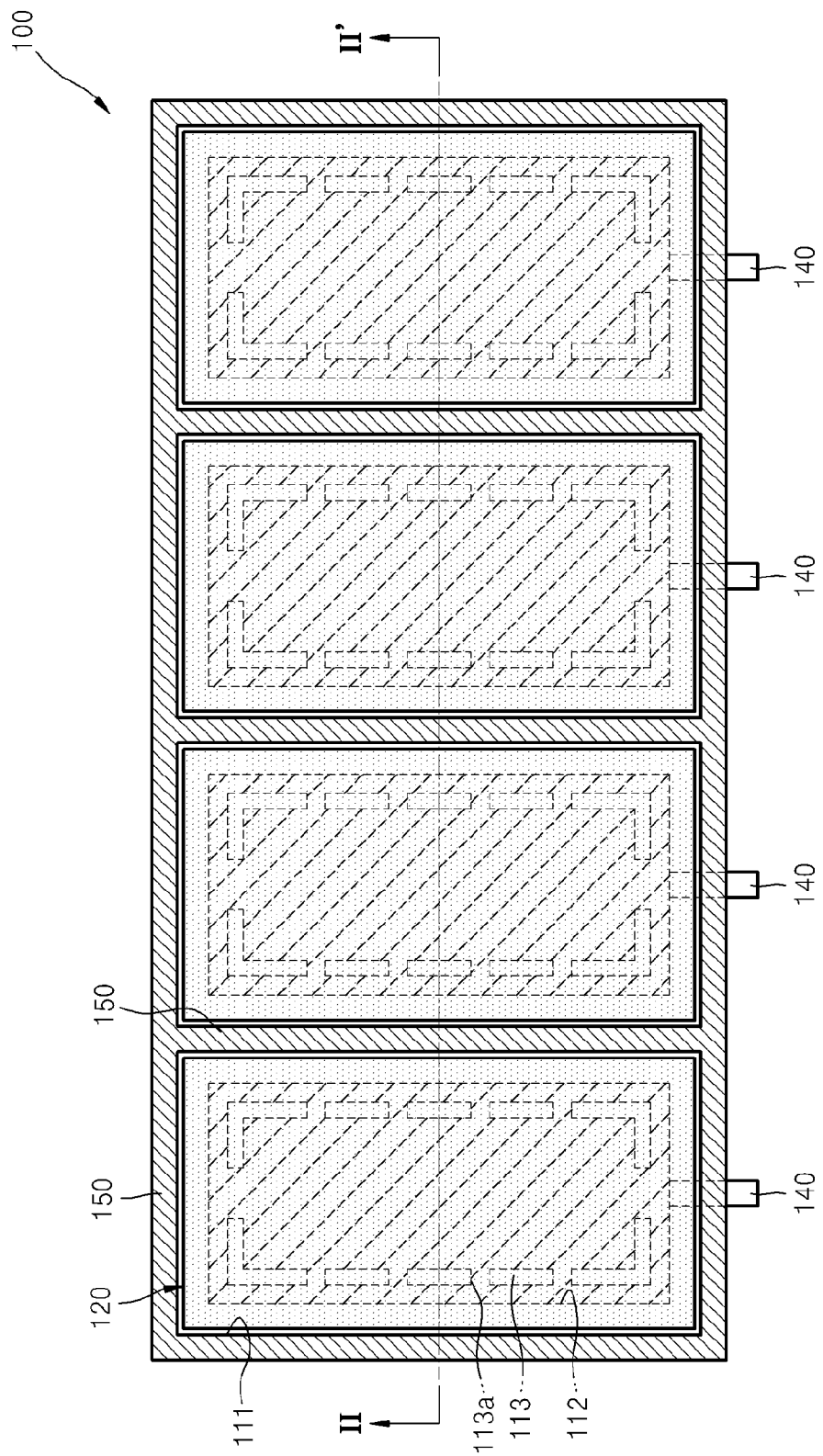
FIG. 1 is a schematic view which illustrates an ultrasonic transducer, according to an exemplary embodiment.

Reference will now be made in detail to exemplary embodiments, examples of which are illustrated in the accompanying drawings, wherein like reference numerals refer to the like elements throughout. In this regard, the present exemplary embodiments may have different forms and should not be construed as being limited to the descriptions set forth herein. Accordingly, the exemplary embodiments are merely described below, by referring to the figures, to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

Figure 2:
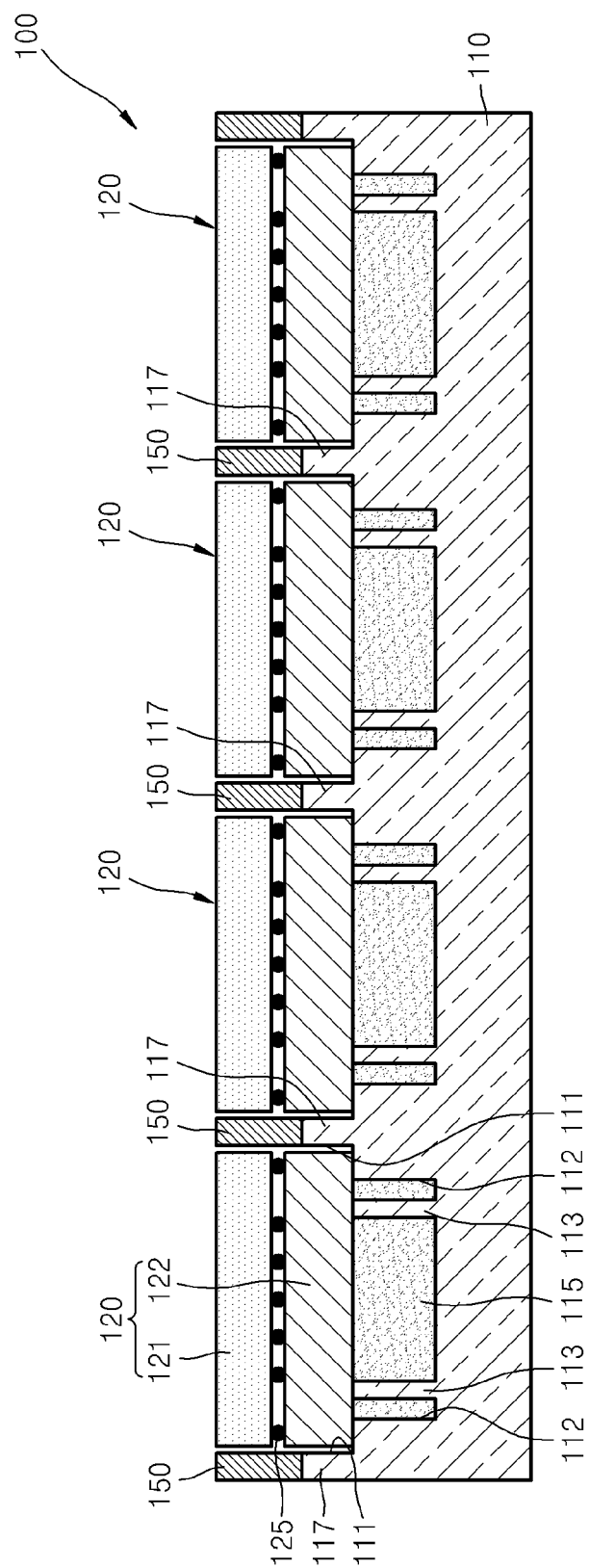
FIG. 2 is a cross-sectional view which illustrates an ultrasonic transducer that is cut along the lines II-II' of FIG. 1.

FIG. 1 is a schematic view which illustrates an ultrasonic transducer, according to an exemplary embodiment. FIG. 2 is a cross-sectional view which illustrates an ultrasonic transducer that is cut along the lines II-II' of FIG. 1.

Referring to FIGS. 1 and 2, an ultrasonic transducer 100 includes a plurality of transducer modules 120, a substrate 110 on which the plurality of transducer modules 120 is arranged, and a buffer member 150 which is arranged on the substrate 110 and which buffers movements of upper portions of the transducer modules 120. FIGS. 1 and 2 illustrate the ultrasonic transducer 100 as including four transducer modules 120 that are arranged on the substrate 110 in a 1×4 array. However, this arrangement is merely one example, and thus, the ultrasonic transducer 100 may include a varying number of the transducer modules 120 in various types of array configurations. Herein, the varying number of the transducer modules 120 may be arranged on the substrate 110 in an m×n array, wherein each of m and n is a natural numbers, in any of various configurations.

Each of the plurality of transducer modules 120 may include an ultrasonic transducer chip 121 and a driver chip 122 that is arranged underneath the ultrasonic transducer chip 121 in order to operate the ultrasonic transducer chip 121. In particular, the ultrasonic transducer chip 121 includes a plurality of ultrasonic conversion elements (not shown) that individually operate to generate one acoustic pulse. A capacitive micromachined ultrasonic transducer (CMUT) chip may be used as the ultrasonic transducer chip 121, and an application specific integrated circuit (ASIC) chip may be used as the driver chip 122. The ultrasonic transducer chip 121 may be deposited on top of the driver chip 122 by performing a flip chip bonding process. A plurality of bonding balls 125 which are used for performing the flip chip bonding process may be arranged between the ultrasonic transducer chip 121 and the driver chip 122. In an exemplary embodiment, the plurality of bonding balls 125 may be placed at irregular spacing intervals in order to facilitate a wiring of a bias signal line and a wiring of a pulse signal line.

The substrate 110 includes a plurality of loaders 111 within which the plurality of transducer modules 120 is loaded and a plurality of adhesive parts 112 which is arranged underneath the plurality of loaders 111. The substrate 100 may include, for example, silicon, glass, and/or a polymer-based material. However, this is merely one example, and thus, the substrate 110 may include a variety of materials in addition to the materials described above. The substrate 110, including the plurality of loaders 111 and the plurality of adhesive parts 112, may be manufactured by using a method of semiconductor processing or imprinting. When the method of semiconductor processing is used, positioning errors relating to the plurality of loaders 111 and adhesive parts 112 may be reduced to within several μm, and accordingly, the plurality of transducer modules 120 that is positioned on the plurality of loaders 111 may be uniformly arranged by adhering to the plurality of adhesive parts 112. Alternatively, when the method of imprinting is used on a silicon substrate, for example, the substrate 110 may be formed of a polymer-based material in order to save production costs and time.

The plurality of loaders 111 is formed on the substrate 110 in correspondence with a number of transducer modules 120 corresponding thereto. The plurality of loaders 111 may be formed at regular spacing intervals (e.g., 20 μm) on the substrate 110. Herein, FIGS. 1 and 2 illustrate the plurality of loaders 111 which correspond to the plurality of transducer modules 120 which are formed on the substrate 110 in an array of 1×4. However, the arrangement is merely one example, and thus, a varying number of the plurality of loaders 111 may be formed on the substrate 110 in a variety of array configurations, such as an m×n array of m×n, wherein each of m and n is a natural number. Due to the plurality of loaders 111, each of the transducer modules 120 may be arranged uniformly in a particular direction. Accordingly, the accuracy of the ultrasonic waves may be increased by controlling directions of transmission/reception of the ultrasonic waves in the plurality of transducer modules 120.

The plurality of loaders 111 may be formed in correspondence with the plurality of transducer modules 120. The plurality of loaders 111 may be formed to a depth of, for example, dozens μm to hundreds μm. The plurality of loaders 111 may be formed with the same depth, and in this case, the plurality of modules 120 which are arranged on the plurality of loaders 111 may be placed at the same relative height with respect to each other. Accordingly, each of the plurality of transducer modules 120 may transmit ultrasonic waves and receive feedback ultrasonic waves from a target object at the same time. Further, in order to control a timing with respect to the transmission/reception of the ultrasonic waves in each of the plurality of transducer modules 120, each of the plurality of loaders 111 may be individually formed to a different respective depth.

In order to load the plurality of transducer modules 120 in the plurality of loaders 111 easily, at least one of the plurality of loaders 111 may be formed to have a width which is wider than a width of one of the plurality of transducer modules 120. For example, a width of at least one of the plurality of loaders 111 may be about 10~20 nm wider than the width of one of the plurality of transducer modules 120, but the width is not limited thereto. When the plurality of transducer modules 120 are loaded in the centers of the plurality of loaders 111, the inner sides of the plurality of loaders 111 may be spaced at regular spacing intervals with respect to the sides of the plurality of transducer modules 120. For example, when the width of at least one of the plurality of loaders 111 is about 10 nm wider than the width of one of the plurality of transducer modules 120, the inner sides of the at least one of the plurality of loaders 111 may be spaced at about 5 nm spacing intervals with respect to the sides of the plurality of transducer modules 120.

On the substrate 110 that is positioned underneath the plurality of loaders 111, a plurality of adhesive parts 112 is formed. Herein, the plurality of adhesive parts 112 is formed in correspondence with the plurality of loaders 111. Such plurality of adhesive parts 112 serves to fix the plurality of transducer modules 120 on the substrate 110 by adhering upper surfaces of each of the plurality of adhesive parts 112 to undersurfaces of the plurality of transducer modules 120. To this end, adhesive materials 115 such as, for example, epoxy may be used for filling in the plurality of adhesive parts 112. The plurality of adhesive parts 112 may be formed to a depth of, for example, dozens of μm to hundreds of μm, but the depth is not limited thereto. The plurality of adhesive parts 112 may be formed with the same depth or with different respective heights. At least one of plurality of adhesive parts 112 may be formed to be narrower than the width of one of the plurality of loaders 111, but the widths of the adhesive parts are not limited thereto.

In each of the plurality of adhesive parts 112, protrusions 113 which protrude from a bottom of at least one of the plurality of adhesive parts 112 may be formed. The protrusions 113 may be integrally formed with the substrate 110. The protrusions 113 may be arranged at regular spacing intervals along an outer part of at least one of the plurality of adhesive parts 112. However, the arrangement is not limited thereto, and the protrusion 113 may be arranged in various forms. Herein, a height of at least one of the protrusions 113 may be identical to the height of one of the plurality of adhesive parts 112. Accordingly, top surfaces of each of the protrusions 113 may be in contact with undersurfaces of each of the plurality of transducer modules 120. Such protrusions 113 reduce a movement of at least one of the plurality of adhesive parts 112 which movement is caused by vibrations that occur during transmission of the ultrasonic waves by each of the plurality of transducer modules 120, and thus, the plurality of transducer modules 120 may be adhered more stably to the substrate 110. After loading the plurality of transducer modules 120 into a space inside of the plurality of loaders 111, followed by attaching the plurality of adhesive parts 112, the adhesive materials 115 which fill in the plurality of adhesive parts 112 inside of the protrusions 113 may be moved to the plurality of adhesive parts 112 outside of the protrusions 113 via through-holes 113a between the protrusions 113 due to the pressure applied by the plurality of transducer modules 120. Accordingly, an arrangement of the plurality of protrusions 113 in the plurality of adhesive parts 112 has been described above, but it is also possible to construct integral protrusions. In addition, a plurality of out ports 140 which connect of the plurality of adhesive parts 112 to an outside of the substrate 110 may further be arranged in the substrate 110. Such out ports 140 may be formed in correspondence with each of the plurality of adhesive parts 112. After loading the plurality of transducer modules 120 into the plurality of loaders 111, the adhesive materials 115 which fill in the plurality of adhesive parts 112 may be released into the outside of the substrate 110 during a process of attaching to the plurality of adhesive parts 112 via the out ports 140 due to pressure applied by the plurality of transducer modules 120.

A supporting part 117 (also referred to herein as a support part 117) protrudes from the substrate 110 between the plurality of loaders 111 and/or from the substrate 110 outside of the plurality of loaders 111. Such supporting part 117 may be integrally formed with the substrate 110. The supporting part 117 may support a lower portion of at least one of the plurality of transducer modules 120. In particular, the supporting part 117 has a lower height than the thickness of at least one of the plurality of transducer modules 120, and thus, the sides of the driver chips 122 may be supported. The supporting part 117 may be formed with the height of, for example, of dozens μm, but is not limited thereto. The supporting part 117 may be formed with a width which is identical to the spacing between the plurality of loaders 111, but is not limited thereto, and may be formed with a width which is narrower than the spacing between the plurality of loaders 111.

On the supporting part 117, a buffer member 150 is arranged. Herein, the buffer member 150 may support the upper portion of at least one of the plurality of transducer modules 120. In particular, the buffer member 150 serves to buffer shocks which result from a movement of at least one of the ultrasonic transducer chips 121 that occurs during the operation of the ultrasonic transducer 100. In general, when the ultrasonic transducer chips 121, which are attached to the fixed driver chips 122, are operated at a low frequency, deformation may be caused due to rotation of the in-plane, thereby resulting in a movement in a horizontal direction. When the ultrasonic transducer chips 121 are operated at a high frequency, deformation may be caused due to distortion on the out-of-plane, thereby resulting in a movement in a vertical direction. In addition, when these deformations increase, the ultrasonic transducer chips 121 that are adjacent to each other may collide with each other.

According to an exemplary embodiment, the buffer member 150 is arranged on the sides of the ultrasonic transducer chips 121 on the supporting part 117 in order to buffer a rotation on the in-plane, that is, the movement of the ultrasonic transducer chips 121 that occurs in a horizontal direction during operation, and thus, deformation of the ultrasonic transducer chips 121 may be reduced. Such a buffer member 150 may include a material which is used to buffer shocks. For example, the buffer member 150 may include a polymer-based material such as epoxy, but is not limited thereto. Due to the buffer member 150, deformation of the ultrasonic transducer chips 121 may be prevented, and accordingly, increased accuracy with respect to ultrasonic transmission and reception become possible. The buffer member 150 may be made by printing a polymer-based material by using a technique such as an imprinting on the supporting part 117 of the substrate 110, which shortens production time and reduces production cost.

Figure 3:
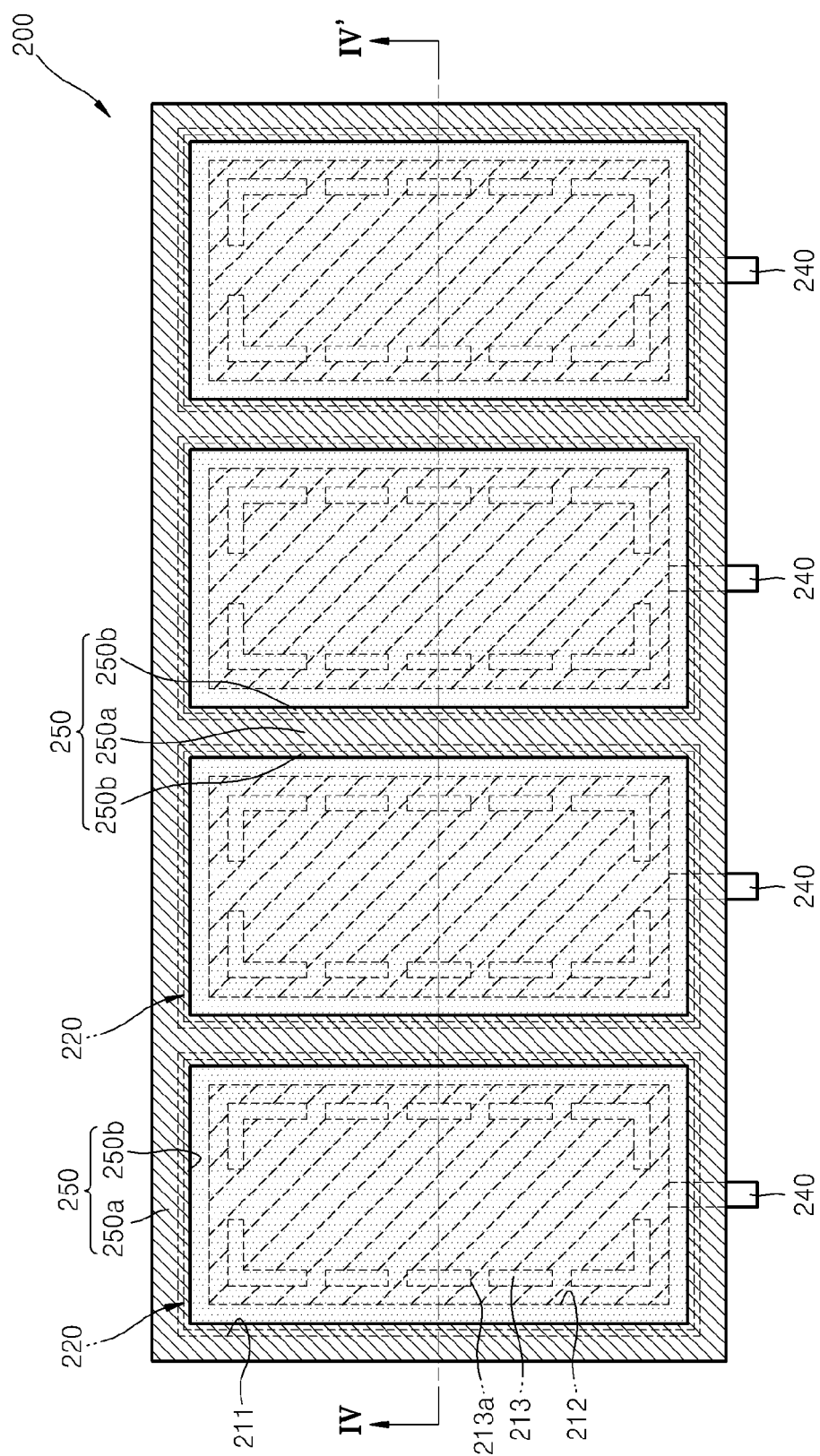
FIG. 3 is a schematic view which illustrates an ultrasonic transducer, according to an exemplary embodiment.
Figure 4:
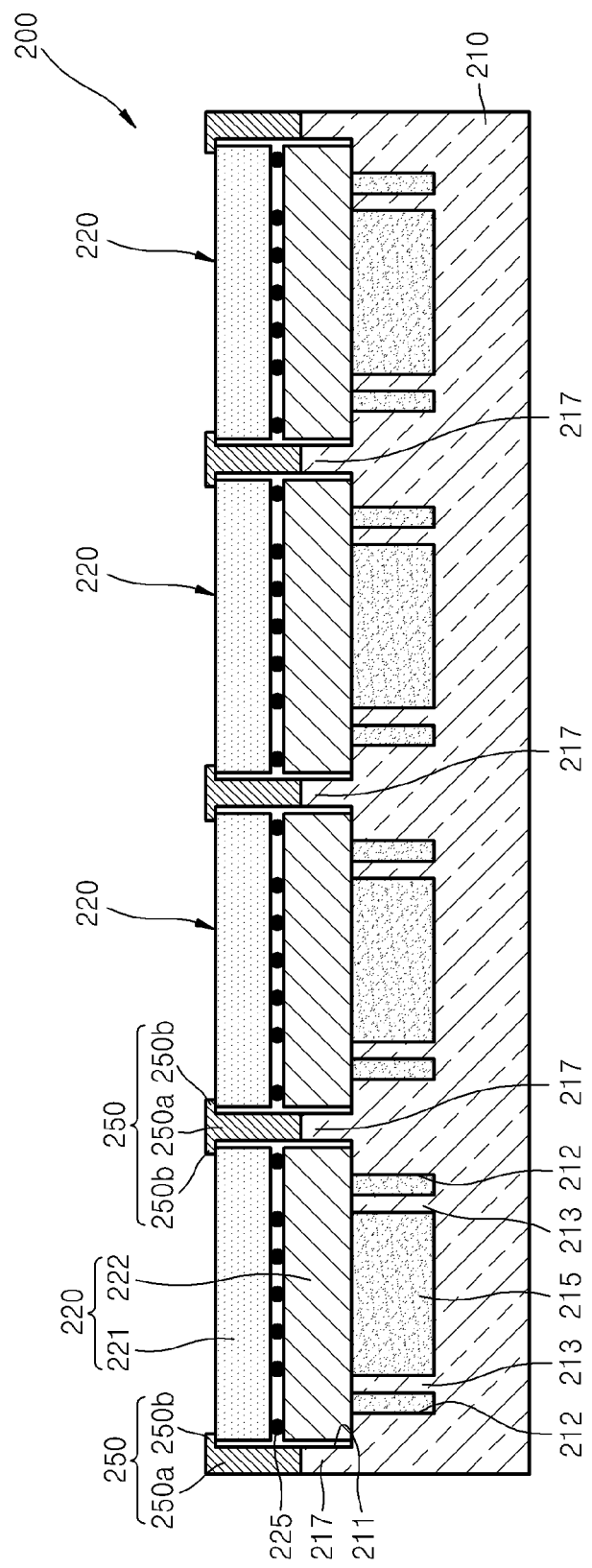
FIG. 4 is a cross-sectional view which illustrates an ultrasonic transducer that is cut along the lines IV-IV' of FIG. 3.

FIG. 3 is a schematic view which illustrates an ultrasonic transducer, according to an exemplary embodiment, and FIG. 4 is a cross-sectional view which illustrates an ultrasonic transducer that is cut along the lines IV-IV' of FIG. 3. Hereinafter, the present exemplary embodiment is described with respect to a different point of focus from the exemplary embodiments described above.

Referring to FIGS. 3 and 4, an ultrasonic transducer 200 includes a plurality of transducer modules 220, a substrate 210 on which the plurality of transducer modules 220 is arranged, a buffer member 250 which is arranged on the substrate 210 and which buffers a movement of an upper portion of at least one of the plurality of transducer modules 220. The ultrasonic transducer 200 may include a varying number of transducer modules 220, and the plurality of transducer modules 220 may be variously arranged on the substrate 210; for example, the plurality of transducer modules 220 may be arranged in an m×n array, wherein each of m and n is a natural number. Each of the plurality of transducer modules 220 may include a driver chip 222 and an ultrasonic transducer chip 221 that is attached to the top of the driver chip 222 via flip chip bonding. A CMUT chip may be used as the ultrasonic transducer chip 221, and an ASIC chip may be used as the driver chip 222. In addition, a plurality of bonding balls 225 which are used for performing flip chip bonding may be provided between the ultrasonic transducer chip 221 and the driver chip 222.

The substrate 210 includes a plurality of loaders 211 within which the plurality of transducer modules 220 are loaded and a plurality of adhesive parts 212 which is arranged underneath the plurality of loaders 211. The substrate 210 may include, for example, at least one of silicon, glass, and a polymer-based material. The plurality of loaders 211 is formed on the substrate 210, and the number of loaders 211 depends on the number of the transducer modules. Each of the plurality of loaders 211 may be formed at regular spacing intervals on the substrate 210. The plurality of loaders 211 may be formed in correspondence with the plurality of transducer modules 220. For example, each of the plurality of loaders 211 may be formed to a depth of dozens of μm to hundreds of μm. Each of the plurality of loaders 211 also may be formed with the same depth or with different depths with respect to each other. In addition, each of the plurality of loaders 211 may be formed to be wider than the each of the plurality of transducer modules 220, in order to facilitate loading of each of the plurality of transducer modules 220 in each of the plurality of loaders 211 easily.

In the substrate 210, which is positioned underneath of the plurality of loaders 211, the plurality of adhesive parts 212 is formed. Herein, the plurality of adhesive parts 212 is formed in correspondence with each of the plurality of loaders 211. An adhesive material 215, such as, for example, epoxy, may be used to fill in the plurality of adhesive parts 212. Each of the plurality of adhesive parts 212 may be formed to a depth of, for example, dozens of μm to hundreds of μm, but the depth is not limited thereto. Each of the plurality of adhesive parts 212 may have the same depth or different depths with respect to each other. In addition, each of the plurality of adhesive parts 212 may be formed to have a width which is smaller than the width of the plurality of loaders 211, but the width is not limited thereto. In each of the plurality of adhesive parts 212, protrusions 213 which protrude from the bottoms of at least one of the plurality of adhesive parts 212 may be arranged. A depth of the protrusions 213 may be the same as a height of at least one of the plurality of adhesive parts 212. Alternatively, in the plurality of adhesive parts 212, protrusions that are integrally formed may be provided. Further, in the substrate 210, a plurality of out ports 240 which connect the plurality of adhesive parts 212 to the outside of the substrate 210 may be arranged.

On the substrate 210, between the plurality of loaders 211 and outside of the plurality of loaders 211, a supporting part 217 is arranged in a protruding form. The supporting part 217 may be integrally formed with the substrate 210. The supporting part 217 may support a lower portion of at least one of the plurality of transducer modules 220. In particular, the supporting part 217 is arranged with a height which is less than the thickness of at least one of the plurality of transducer modules 220, and thus, the supporting part 217 may be able to support the driver chips 222. The supporting part 217 may be formed to a height of, for example, dozens of μm, but the height is not limited thereto. In addition, the supporting part 217 may be formed with a width which is equal to or less than a spacing between the plurality of loaders 211.

On top of the supporting part 217, a buffer member 250 is provided. Herein, the buffer member 250 may be able to support the upper portion of at least one of the plurality of transducer modules 220. The buffer member 250 may include a first buffer part 250a which is positioned on the sides of the ultrasonic transducer chips 221 and a second buffer part 250b which extends from the first buffer part 250a toward the upper surface of at least one of the ultrasonic transducer chips 220. Herein, the first buffer part 250a may buffer the movements of the ultrasonic transducer chips 220 in a horizontal direction, which result from a rotation on the in-plane that occurs during the operation of the ultrasonic transducer chips 220. Further, the second buffer part 250b may buffer the movements of the ultrasonic transducer chips 220 in a vertical direction, which result from a distortion on the out-of-plane that occurs during the operation of the ultrasonic transducer chips 220. Accordingly, the buffer member 250 may reduce a deformation of at least one of the ultrasonic transducer chips 221 which results from rotation on the in-plane and distortion on the out-of-plane. The buffer member 250 may include a polymer-based material, such as, for example, epoxy, but the material is not limited thereto. Therefore, according to the present exemplary embodiment, the buffer member 250 may be able to buffer not only rotation on the in-plane, but also distortion on the out-of-plane; thus, deformation of the ultrasonic transducer chips 221 may be prevented more efficiently, thereby providing a more accurate ultrasonic transmission and/or reception.

Figure 5:
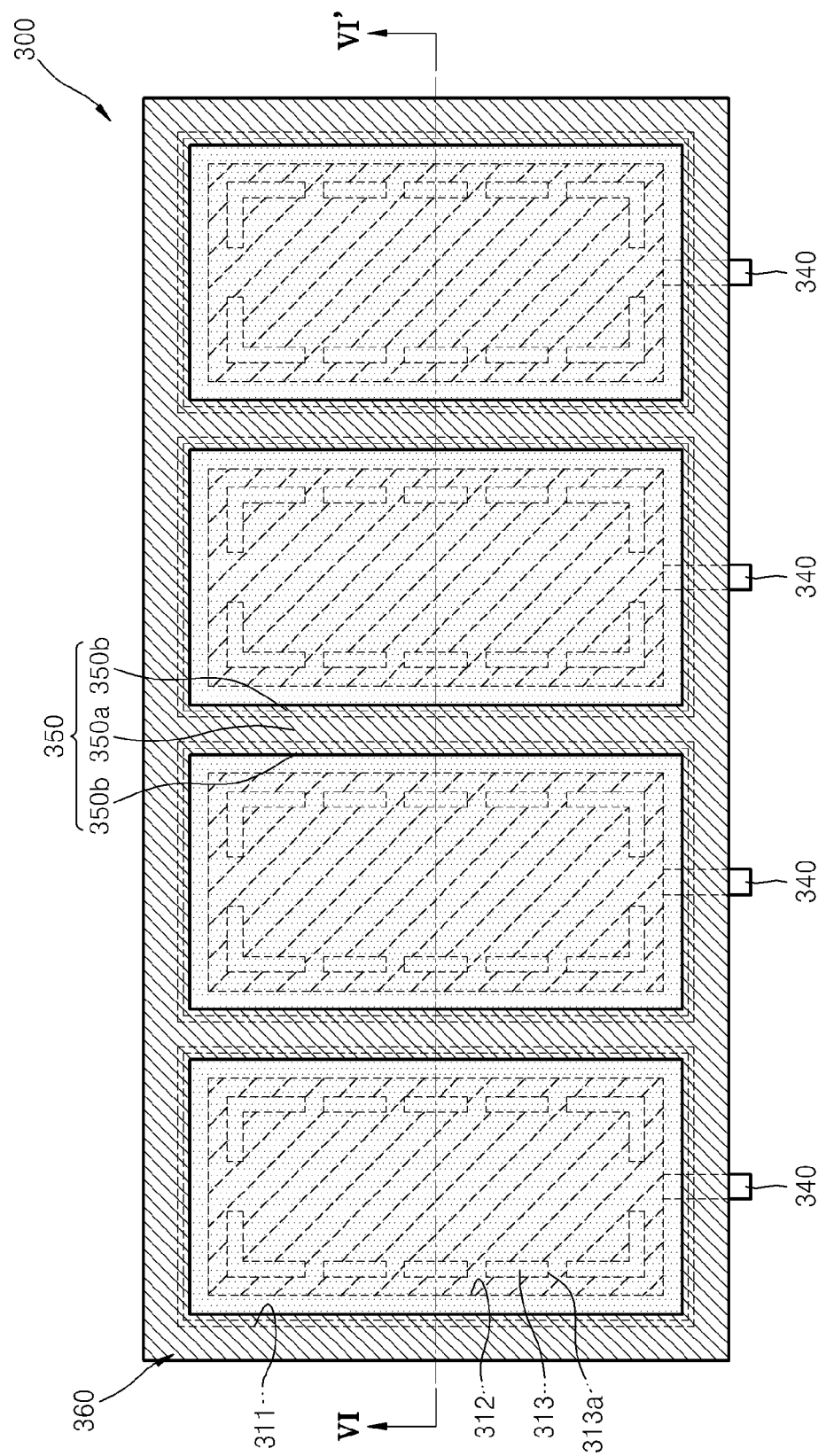
FIG. 5 is a schematic view which illustrates an ultrasonic transducer, according to an exemplary embodiment.
Figure 6:
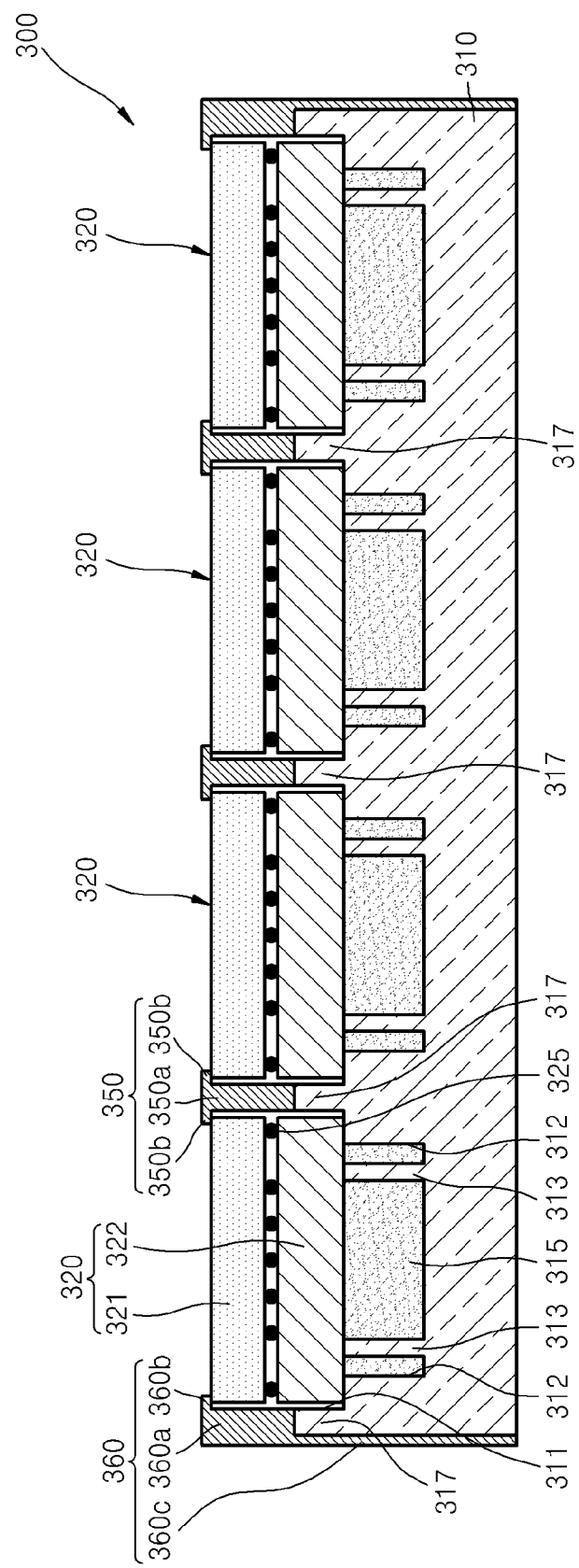
FIG. 6 is cross-sectional view which illustrates an ultrasonic transducer that is cut along the lines VI-VI' of FIG. 5.

FIG. 5 is a schematic view which illustrates an ultrasonic transducer, according to an exemplary embodiment, and FIG. 6 is cross-sectional view which illustrates an ultrasonic transducer that is cut along the lines VI-VI' of FIG. 5.

Referring to FIGS. 5 and 6, an ultrasonic transducer 300 includes a plurality of transducer modules 320, a substrate 310 on which the plurality of transducer modules 320 is arranged, and a buffer member 350 which is arranged on the substrate 310 and which buffers the movements of an upper portion of at least one of the plurality of transducer modules 320. Each of the plurality of transducer modules 320 may include a driver chip 322 and an ultrasonic transducer chip 321 that is attached to the top of the driver chip 322 via flip chip bonding. A CMUT chip may be used as the ultrasonic transducer chip 321, and an ASIC chip may be used as the driver chip 322. In addition, a plurality of bonding balls 325 which are used for flip chip bonding may be provided between at least one ultrasonic transducer chip 321 and at least one corresponding driver chip 322.

The substrate 310 includes a plurality of loaders 311 within which the plurality of transducer modules 320 is loaded and a plurality of adhesive parts 312 which is arranged underneath the plurality of loaders 311. Each of the plurality of loaders 311 may be formed with the same depth or with different depths with respect to each other. In addition, each of the plurality of loaders 311 may be formed to have a width which is wider than the width of at least one of the plurality of transducer modules 320. In the substrate 310 underneath of the plurality of loaders 311, the plurality of adhesive parts 312 is formed. An adhesive material 315, such as, for example, epoxy, may be used to fill in the plurality of adhesive parts 312. Each of the plurality of adhesive parts 312 may have the same depth or a different depth with respect to each other. In addition, each of the plurality of adhesive parts 312 may be formed to have a width which is smaller than the width of at least one of the plurality of loaders 311, but the width is not limited thereto. In each of the plurality of adhesive parts 312, protrusions 313 which protrude from the bottoms of the plurality of adhesive parts 312 may be provided. Depth of the protrusions 313 may be the same as a height of each of the plurality of adhesive parts 312. Further, in the substrate 310, a plurality of out ports 340 which connect the plurality of adhesive parts 312 to the outside of the substrate 310 may be arranged.

On the substrate 310, between the plurality of loaders 311 and outside the plurality of loaders 311, a supporting part 317 is arranged in a protruding form. The supporting part 317 is arranged with a height which is less than the thickness of at least one of the plurality of transducer modules 320, and thus, the supporting part 317 may be able to support the driver chips 322. In addition, the supporting part 317 may be formed with a width which is equal to or less than a spacing between the plurality of loaders 311.

On top of the supporting part 317, a buffer member 350 is provided. Herein, the buffer member 350 may be able to support the upper portion of at least one of the plurality of transducer modules 320. The buffer member 350 includes a first buffer member which is arranged between the ultrasonic transducer chips 320 and a second buffer member 360 which is arranged outside of the ultrasonic transducer chips 320. The first buffer member 350 may include a first buffer part 350*a* which is positioned on the sides of the ultrasonic transducer chips 320 and a second buffer part 350*b* which extends from the first buffer part 350*a* toward the upper surface of at least one of the ultrasonic transducer chips 320. Herein, the first buffer part 350*a* may buffer the movements of the ultrasonic transducer chips 320 in a horizontal direction, which result from a rotation on the in-plane that occurs during the operation of the ultrasonic transducer chips 320. Further, the second buffer part 350*b* may buffer the movements of the ultrasonic transducer chips 320 in a vertical direction, which result from a distortion on the out-of-plane that occurs during the operation of the ultrasonic transducer chips 320. In addition, the second buffer member 360 may include a first buffer part 360*a* which is positioned on the sides of the ultrasonic transducer chips 320, a second buffer part 360*b* which extends from the first buffer part 350*a* toward the upper surface of at least one of the ultrasonic transducer chips 320*b*, and a third buffer part 360*c* which extends from the first buffer part 360*a* toward the outside of the substrate 310. Herein, the first buffer part 360*a* may buffer a rotation on the in-plane of the ultrasonic transducer chips 320, and the second buffer part 360*b* may buffer a distortion on the out-of-plane of the ultrasonic transducer chips 320. Therefore, deformation of the ultrasonic transducer chips 320 due to the rotation on the in-plane and distortion on the out-of-plane are reduced, and thus, increased accuracy of ultrasonic transmission and/or reception become possible. According to the present exemplary embodiment, the third buffer part 360*c* is formed to surround the end sides of the substrate 310, thus, the second buffer member 360 may be more firmly formed on the substrate 310, as compared to the exemplary embodiment described above.

As described above, the buffer members may be provided between the ultrasonic transducer chips and outside of the ultrasonic transducer chips. The movements of the ultrasonic transducer chips in horizontal and vertical directions that may occur during the operation of the ultrasonic transducer chips may be buffered, and thus, deformation of ultrasonic transducer chips may be prevented. Accordingly, the ultrasonic transducer chips may perform more accurate ultrasonic transmission/reception. Further, buffer members may be prepared on a substrate in a short time at a low cost by forming a polymer-based material by using an imprinting technology.

It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.

What is claimed is:

1. An ultrasonic transducer comprising:
a plurality of transducers;
a substrate on which the plurality of transducers is arranged; and
a buffer member which buffers movements of upper portions of the transducers,
wherein the buffer member is disposed on the substrate between adjacent transducers within the plurality of transducers and on the substrate outside of the plurality of transducers.

2. The ultrasonic transducer of claim 1, wherein each of the plurality of transducers comprises an ultrasonic transducer chip and a driver chip which is arranged underneath the ultrasonic transducer chip.

3. The ultrasonic transducer of claim 2, wherein the ultrasonic transducer chip comprises a capacitive micromachined ultrasonic transducer chip, and the driver chip comprises an application-specific integrated circuit (ASIC) chip.

4. The ultrasonic transducer of claim 2, wherein the substrate comprises a plurality of loaders in which the plurality of transducers are loaded, a plurality of adhesive parts which are arranged underneath the plurality of loaders such that top surfaces of the plurality of adhesive parts are adhered to undersurfaces of the plurality of transducers, and a support part which protrudes between the plurality of loaders and outside of the plurality of loaders.

5. The ultrasonic transducer of claim 4, wherein the support part supports the driver chips.

6. The ultrasonic transducer of claim 5, wherein the buffer member buffers movements of the ultrasonic transducer chips on a top surface of the support part.

7. The ultrasonic transducer of claim 6, wherein the buffer member comprises at least one polymer-based material.

8. The ultrasonic transducer of claim 6, wherein the buffer member comprises a first buffer part which is arranged on a side of at least one of the ultrasonic transducer chips and a second buffer part which extends from the first buffer part toward an upper surface of at least one of the ultrasonic transducer chips.

9. The ultrasonic transducer of claim 6, wherein the buffer member comprises a first buffer member which is arranged between the ultrasonic transducer chips and a second buffer member which is arranged outside of the ultrasonic transducer chips.

10. The ultrasonic transducer of claim 9, wherein the first buffer member comprises a first buffer part which is arranged on a side of at least one of the ultrasonic transducer chips and a second buffer part which extends from the first buffer part toward an upper surface of at least one of the ultrasonic transducer chips.

11. The ultrasonic transducer of claim 9, wherein the second buffer member comprises a first buffer part which is arranged on a side of at least one of the ultrasonic transducer chips, a second buffer part which extends from the first buffer part toward an upper surface of at least one of the ultrasonic transducer chips, and a third buffer part which extends from the first buffer part toward an outside of the substrate.

12. The ultrasonic transducer of claim 4, wherein one of the plurality of loaders has a width which is wider than a width of a corresponding one of the plurality of transducers, and one of the plurality of adhesive parts has a width which is narrower than the width of at least one of the plurality of loaders.

13. The ultrasonic transducer of claim 4, wherein the plurality of adhesive parts is filled with adhesive materials.

14. The ultrasonic transducer of claim 13, wherein a plurality of out ports which connect the plurality of adhesive parts to an outside of the substrate is formed in the substrate.

15. The ultrasonic transducer of claim 4, wherein at least one of protrusions which protrude from a bottom of one of the plurality of adhesive parts is formed in each of the plurality of adhesive parts.

16. The ultrasonic transducer of claim 15, wherein at least one of the protrusions comprises a top side which adheres to an undersurface of at least one of the plurality of transducers.

17. The ultrasonic transducer of claim 15, wherein at least one of the protrusions is integrally formed with the substrate.

18. The ultrasonic transducer of claim 15, wherein at least one of the protrusions comprises a plurality of protrusions that are spaced at a predetermined spacing.

19. The ultrasonic transducer of claim 1, wherein the substrate comprises at least one of silicon, a glass, and a polymer-based material.

20. The ultrasonic transducer of claim 1, wherein the plurality of transducers are arranged on the substrate in an m×n array, wherein each of m and n is a natural number.

21. A method for manufacturing an ultrasonic transducer, the method comprising:
   arranging a plurality of transducers on a substrate; and
   arranging a buffer member which buffers movements of upper portions of the transducers,
   wherein the buffer member is disposed on the substrate between adjacent transducers within the plurality of transducers and on the substrate outside of the plurality of transducers.

22. The method of claim 21, wherein each of the plurality of transducers comprises an ultrasonic transducer chip and a driver chip which is arranged underneath the ultrasonic transducer chip.

23. The method of claim 22, wherein the ultrasonic transducer chip comprises a capacitive micromachined ultrasonic transducer chip, and the driver chip comprises an application-specific integrated circuit (ASIC) chip.

24. The method of claim 22, further comprising:
   arranging, on the substrate, a plurality of loaders in which the plurality of transducers are loaded;
   arranging, on the substrate, a plurality of adhesive parts which are arranged underneath the plurality of loaders such that top surfaces of the adhesive parts are adhered to undersurfaces of the transducers; and
   arranging, on the substrate, a support part which protrudes between the plurality of loaders and outside of the plurality of loaders.

25. The method of claim 24, wherein the support part supports the driver chips.

* * * * *